US00PP12227P2

(12) United States Plant Patent
Vandenberg

(10) Patent No.: US PP12,227 P2
(45) Date of Patent: Nov. 27, 2001

(54) CHRYSANTHEMUM PLANT NAMED 'YOBUTTERFIELD'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/525,654

(22) Filed: Mar. 15, 2000

(51) Int. Cl.[7] ..... A01H 5/00
(52) U.S. Cl. ..... Plt./295
(58) Field of Search ..... Plt./295

*Primary Examiner*—Howard J. Locker
(74) *Attorney, Agent, or Firm*—C. A. Whealy

(57) ABSTRACT

A distinct cultivar of Chrysanthemum plant named 'Yobutterfield', characterized by its upright and uniformly mounded plant habit; freely branching, dense and full plants; strong dark green foliage; uniform flowering; early flowering, eight-week response time; very freely flowering with about seven or eight inflorescences per lateral stem; large daisy-type inflorescences that are about 8.2 cm in diameter; bright yellow-colored ray florets and darker yellow disc florets; and excellent postproduction longevity with inflorescences and leaves maintaining good substance and color for about three to four weeks in an interior environment.

2 Drawing Sheets

BACKGROUND OF THE INVENTION

The present Invention relates to a new and distinct cultivar of Chrysanthemum plant, botanically known as *Dendranthema grandiflora* and hereinafter referred to by the cultivar name Yobutterfield.

The new Chrysanthemum is a product of a planned breeding program conducted by the Inventor in Salinas, Calif. The objective of the breeding program is to create new potted Chrysanthemum cultivars with desirable inflorescence form and floret colors, good substance, and excellent postproduction longevity.

The new Chrysanthemum originated from a cross made by the Inventor in May, 1993, in Salinas, Calif., of a proprietary Chrysanthemum seedling selection identified as YB-6496 as the male, or pollen, parent with a proprietary Chrysanthemum seedling selection identified as YB-6370 as the female, or seed, parent. The new Chrysanthemum was discovered and selected by the Inventor as a single flowering plant within this population in March, 1994. The selection of this plant was based on its desirable inflorescence form and floret colors.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yobutterfield has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yobutterfield'. These characteristics in combination distinguish 'Yobutterfield' as a new and distinct Chrysanthemum:

1. Upright and uniformly mounded plant habit.
2. Freely branching, dense and full plants.
3. Strong dark green foliage.
4. Uniform flowering.
5. Early flowering, eight-week response time.
6. Very freely flowering; about seven or eight inflorescences per lateral stem.
7. Large daisy-type inflorescences that are about 8.2 cm in diameter.
8. Bright yellow-colored ray florets and darker yellow disc florets.
9. Excellent postproduction longevity with inflorescences and leaves maintaining good substance and color for about three to four weeks in an interior environment.

Compared to plants of the cultivar, Miramar, disclosed in U.S. Plant Pat. No. 7,469, plants of the are different in the following characteristics:

1. Plants of the new Chrysanthemum have smaller inflorescences than plants of the cultivar Miramar.
2. Plants of the new Chrysanthemum have a more attractive inflorescence form that plants of the cultivar Miramar.
3. Plants of the new Chrysanthemum have broader ray florets than plants of the cultivar Miramar.
4. Plants of the new Chrysanthemum flower about one week earlier than plants of the cultivar Miramar.
5. Plants of the new Chrysanthemum produce much less or no pollen compared to plants of the cultivar Miramar.
6. Plants of the new Chrysanthemum are more upright and not as outwardly spreading as plants of the cultivar Miramar.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the first sheet comprises a side perspective view of a typical flowering plant of 'Yobutterfield'. The photograph at the bottom of the first sheet comprises a close-up view of upper (left) and lower (right) surfaces of typical inflorescences and upper (left) and lower (right) surfaces of typical leaves of the cultivar Yobutterfield.

The photograph at the top of the second sheet comprises a side perspective view of typical flowering plants of 'Yobutterfield' (left) and 'Miramar' (right). The photograph at the bottom of the second sheet comprises a close-up view of typical inflorescences of plants of 'Yobutterfield' (left) and 'Miramar' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the Autumn in Leamington, Ontario, Canada, under greenhouse conditions which approximate those generally used in commercial potted Chrysanthemum production. Four unrooted cuttings were directly stuck in a 15-cm container and pinched once. Plants used for this description were grown as center budded-types. Measurements and numerical values represent averages of typical flowering plants.

Botanical classification: *Dendranthema grandiflora* cultivar Yobutterfield.

Commercial classification: Daisy center budded-type potted Chrysanthemum.

Parentage:

*Male, or pollen, parent.*—Proprietary Chrysanthemum seedling selection identified as YB-6496.

*Female, or seed, parent.*—Proprietary Chrysanthemum seedling selection identified as YB-6370.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy potted Chrysanthemum typically grown as a center budded-type. Inverted triangle; stems mostly upright and somewhat outwardly spreading giving a uniformly mounded appearance to the plant. Freely branching; about three to four lateral branches develop after removal of terminal apex (pinching); dense and full plants.

*Plant height.*—About 29 cm.

*Plant width.*—About 37 cm.

*Foliage description.*—Arrangement: Alternate. Length: About 7.1 cm. Width: About 5.5 cm. Apex: Cuspidate. Base: Cuneate to truncate. Margin: Palmately lobed, sinuses between lateral lobes parallel to divergent. Texture: Upper and lower surfaces with very fine pubescence; veins prominent on lower surface. Petiole length: About 2.25 cm. Petiole diameter: About 3 mm. Color: Young foliage upper surface: Darker than 147A, glossy. Young foliage lower surface: Darker than 147B. Mature foliage upper surface: 147A, glossy. Mature foliage lower surface: 147B. Venation upper surface: 147A. Venation lower surface: 147B.

Inflorescence description:

*Appearance.*—Daisy inflorescence form with elongated oblong-shaped ray florets. Inflorescences borne on terminals above foliage. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences and leaves maintain good color and substance for about three to four weeks in an interior environment.

*Quantity of inflorescences.*—Very freely flowering; about seven to eight inflorescences per lateral stem and about 26 inflorescences per plant.

*Inflorescence bud.*—Height: About 7 mm. Diameter: About 7 mm. Color: Close to 137A.

*Inflorescence size.*—Diameter: About 8.2 cm. Depth (height): About 2.5 cm. Diameter of disc: About 1.6 cm.

*Ray florets.*—Shape: Elongated-oblong. Orientation: Initially upright, then about 45° to horizontal to eventually horizontal. Length: About 3.9 cm. Width: About 1.3 cm. Apex: Mostly rounded to occasionally cuspidate. Margin: Entire. Texture: Smooth, glabrous, satiny. Number of ray florets per inflorescence: About 20. Color: When opening: Brighter yellow than 7A and 5A. Fully opened, upper surface: Brighter yellow than 7A and 5A. Fully opened, lower surface: 7A to 7B.

*Disc florets.*—Shape: Tubular. Apex: Serrated. Length: About 6 mm. Width: Apex and base, about 1 mm. Number of disc florets per inflorescence: About 123. Color: Immature: 144A to 9A. Mature: Apex: Yellow, 9A. Mid-section: Light green, 154D. Base: White, 155D.

*Peduncles.*—Aspect: Angled about 40 to 45° to stem. Length: First peduncle: About 3.9 cm. Fourth peduncle: About 6.5 cm. Diameter: About 3 mm. Texture: Pubescent. Color: 146A.

*Reproductive organs.*—Androecium: Present on disc florets only. Anther color: 9A. Pollen amount: None observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yobutterfield', as illustrated and described.

* * * * *

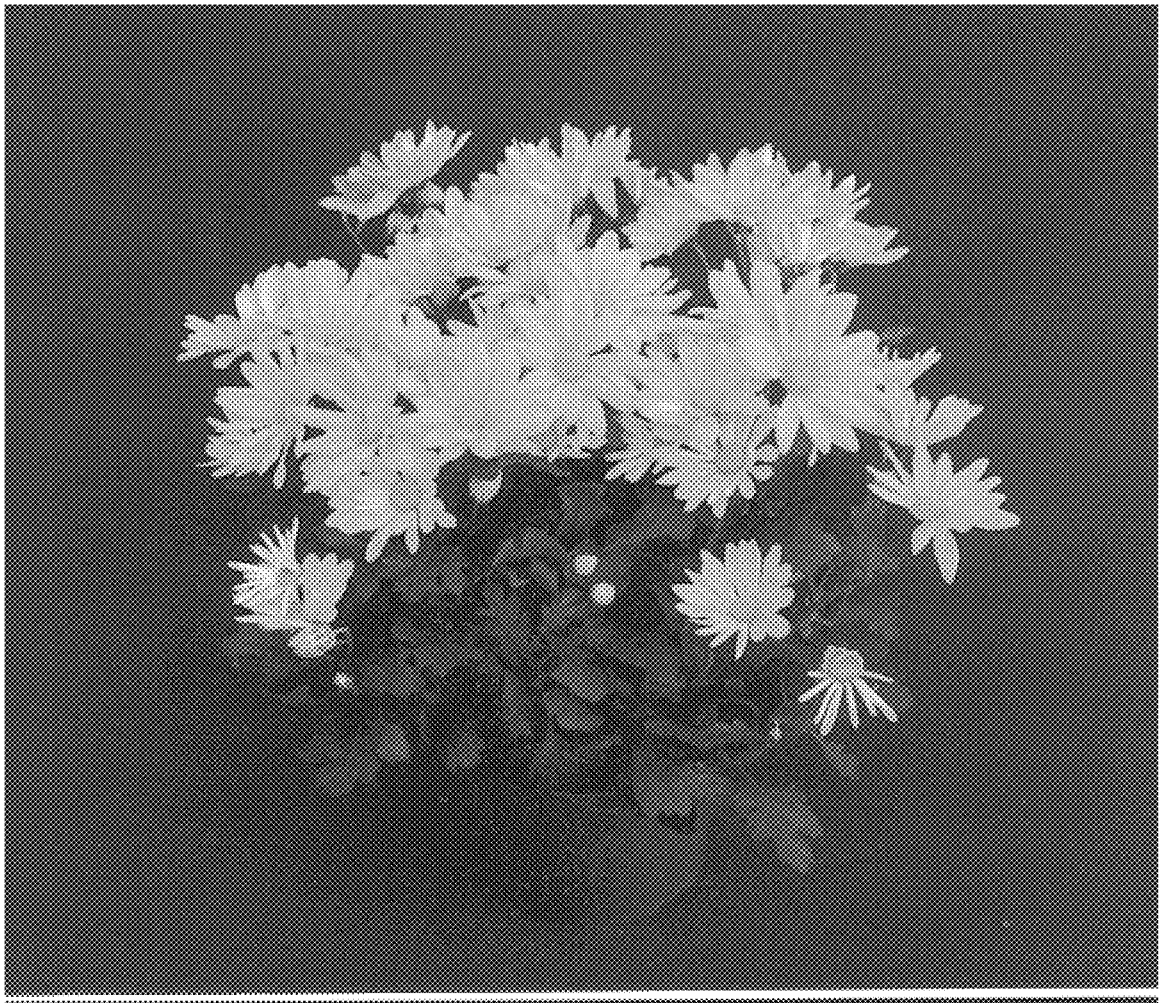
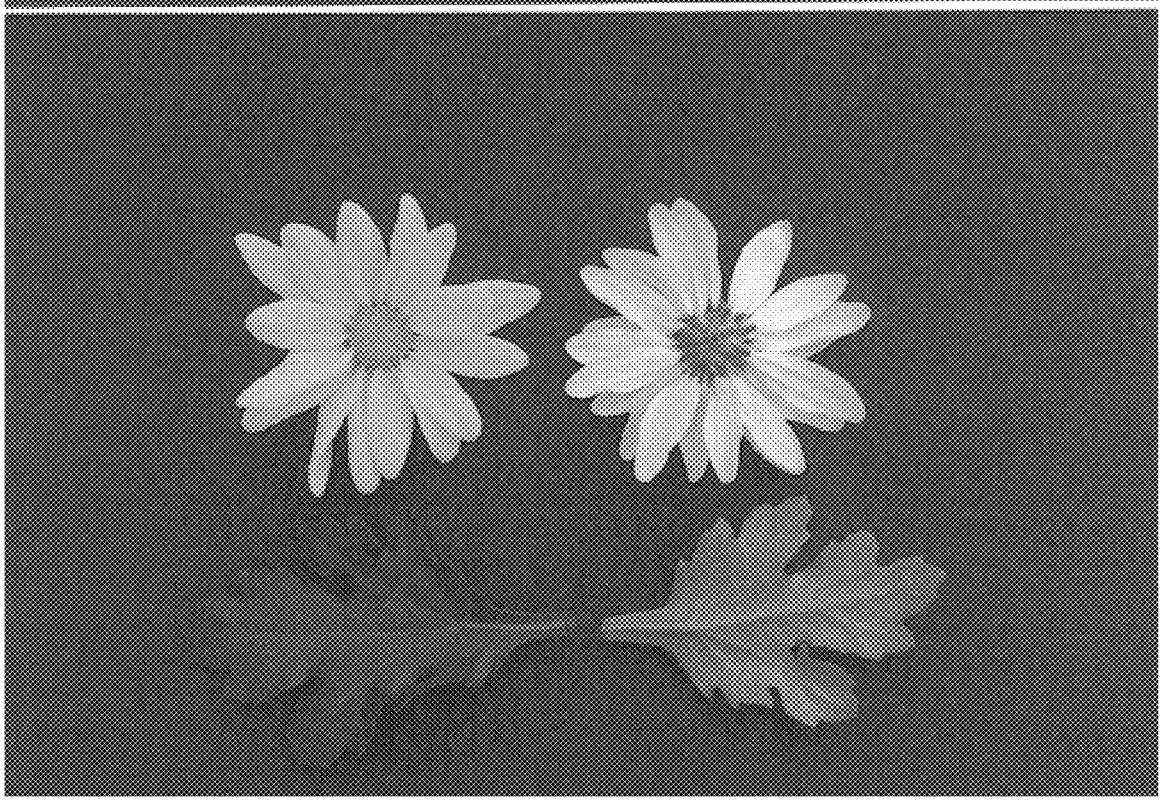

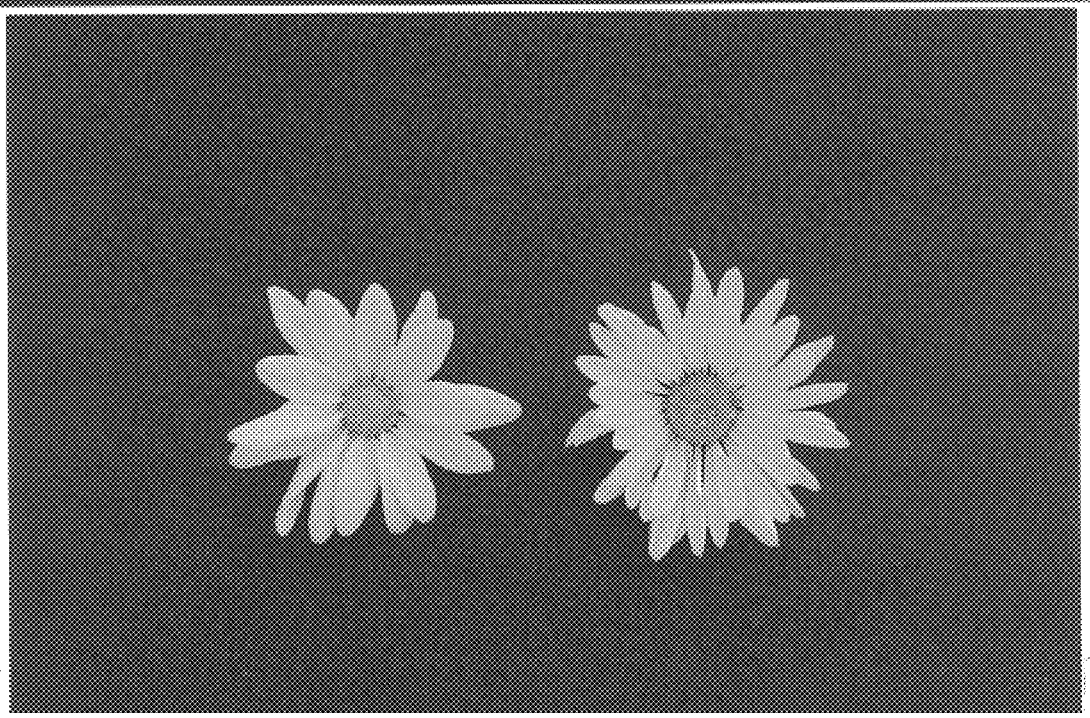

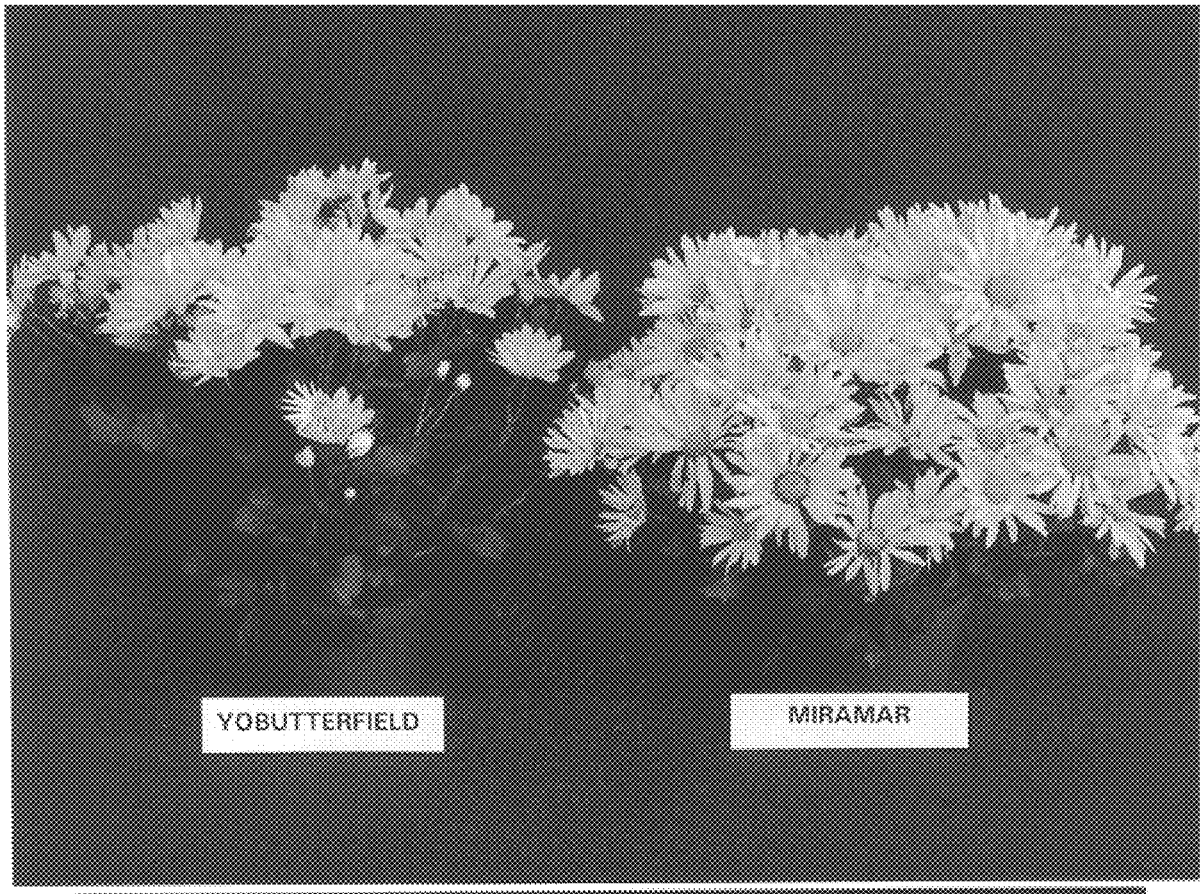
YOBUTTERFIELD
MIRAMAR